United States Patent [19]

Leslie

[11] 4,366,310

[45] Dec. 28, 1982

[54] CONTROLLED RELEASE COMPOSITIONS

[75] Inventor: Stewart T. Leslie, Aberdeen, Scotland

[73] Assignee: Euroceltique, S.A., Luxembourg

[21] Appl. No.: 214,625

[22] Filed: Dec. 10, 1980

[30] Foreign Application Priority Data

Dec. 19, 1979 [IE] Ireland .................................. 2480/79
Dec. 19, 1979 [IE] Ireland .................................. 2481/79

[51] Int. Cl.³ ............................................. C08B 11/00
[52] U.S. Cl. ...................................... 536/56; 106/170; 424/19; 536/84; 536/95; 536/96
[58] Field of Search .................... 426/3, 4, 5; 424/19; 536/56, 84, 95, 96; 106/170

[56] References Cited

U.S. PATENT DOCUMENTS

| | | | |
|---|---|---|---|
| 3,818,107 | 6/1974 | Yolles | 426/3 |
| 3,899,439 | 9/1975 | Mahlman | 106/203 |
| 3,988,482 | 10/1976 | Higashiyama et al. | 424/49 |
| 4,137,399 | 1/1979 | Hulsmann et al. | 536/84 |
| 4,226,849 | 10/1980 | Schor | 424/19 |
| 4,235,870 | 11/1980 | Leslie | 424/19 |
| 4,258,179 | 3/1981 | Kawata et al. | 106/170 |
| 4,259,314 | 3/1981 | Lowey | 424/19 |
| 4,259,355 | 3/1981 | Marmo et al. | 426/5 |
| 4,264,766 | 4/1981 | Fischer | 536/56 |

FOREIGN PATENT DOCUMENTS

1405088  9/1975  United Kingdom .................. 424/19

*Primary Examiner*—Ronald W. Griffin
*Attorney, Agent, or Firm*—Steinberg & Raskin

[57] ABSTRACT

Molecular coordination complexes are formed between a cellulose polymer and a non-polar solid aliphatic alcohol containing 8 to 18 carbon atoms optionally substituted with an aliphatic group containing 8 to 18 carbon atoms by solvating the polymer with a volatile polar solvent and reacting the solvated cellulose polymer directly with the aliphatic alcohol, preferably as a melt. The resulting composition may be dried. This constitutes the complex. The composition has utility as a matrix in controlled release formulations since it has a uniform porosity which may be varied.

11 Claims, No Drawings

CONTROLLED RELEASE COMPOSITIONS

This invention relates to molecular coordination complexes which can also be regarded as matrixes made up by two components bonded together. These complexes or matrixes are porous semi-permeable compositions the particular utility of which is in controlled release formulations, where the release of an active ingredient, for example a pharmaceutical can be controlled.

One component of the complex or matrix is a cellulose polymer and the other is a solid aliphatic alcohol.

As is known cellulose polymer comprises a polysaccharide chain in which the glucosidal units are linked through an oxygen atom. The cellulose polymers contain both crystalline and amorphous areas. The crystalline areas are essentially unreactive and are formed by cross-linkage through hydrogen-bonding between cellulose polymer strands. The amorphous regions are not cross-linked but contain active hydrophilic centres capable of further reaction through hydrogen-bonding. These amorphous centres are generally involved with polymer solvation reactions to form a new hydrogen-bonded compound. The spacing between the amorphous and crystalline areas being maintained by rigid hydrogen-bonded cross-linkage, the crystalline areas and the non-linked open amorphous areas tend to form flexible spaces or pores in the cellulose polymer strand matrix. The size, shape and number of such spaces or pores are determined by the number and linear spacing of the crystalline areas, the number and spacing of amorphous areas and the level of desegregation of the cellulose polymer strand aggregate. These characteristics determine the properties of a particular cellulose polymer and are reflected in the degree of swelling of the solvated cellulose polymer when these agents are utilized in particular formulations.

It is well known that cellulose polymers swell to increase viscosity and provide a thixotropic structure to a colloid dispersions through a solvation reaction with the solvent system used. However, these physical characteristics contributed by the polymers to the solution are dynamic changing properties which increase or decrease in strength as a result of the degree and extent of solvation of the cellulose polymer by the solvent in the system used. In the dry non-solvated state the cellulose polymer strand is contracted and occupies a minimal volume and in the fully solvated state it occupies its greatest volume. The spacing between the crystalline areas and the amorphous areas which contain the reactive hydrophilic centers of the cellulose strand also varies in relation to the solvation of the cellulose strand and is at its contracted level when the polymer is in the dried state but expands in the solvated state. It is the distance between the respective crystalline and amorphous areas, together with the spacing between reactive hydrophilic centers that are reflected in the properties contributed by the polymer to a particular colloidal system and these are expressed by the viscosity, thixotropy and the strength of the structural matrix formed. Thus the contracted non-solvated cellulose polymer chain possesses properties entirely different from the solvated strand. This is readily discernible when the properties of the dry, free-flowing, non-solvated cellulose polymer are compared with those of the dry solvated solid cellulose polymer.

When a polar solvent is brought into contact with a cellulose polymer it permeates the polymer strand causing it to swell through a solvation reaction involving the hydrophilic centres of the amorphous area. The effect of such solvation on the polymer strand aggregate first results in an increased viscosity as a volume response to the expanded polymer chain which now occupies a greater volume in solution. As the solvation continues the effective polymer solution volume/viscosity increases. However, when the solvated polymer chains are forced further apart, thereby increasing the distance between all active centers beyond the strand structure strength, then the strand begins to desegregate. When desegregation occurs the oberved viscosity increase begins to be neutralized and is even reversed. If the solvation reaction continues beyond the full solution-solvation state and the polymer strand completely desegregates, each polymer chain now becomes individually coated with solvent. This blocks the reactive centers of the chain and destroys the particular pore-matrix structure of the respective polymer thereby eliminating the ability of the polymer to influence the properties of the solvent. Thus for example a reduction in viscosity will be observed for a desegregated polymer in colloidal dispersion rather than a continuing increase in viscosity, as the solvation reaction continues beyond the full solution solvation level.

Upon aging or solvent-depletion as for example during drying, a reversion to the presolvated polymer state occurs to modify the overall properties of the system in solution. This change in properties of the polymer-solvent system is proportional to the extent of modification achieved and to the extent of desegregation which had occurred. When polar solvents such as water, glycerin, sorbitol and other solvents of a similar nature are used to solvate a cellulose polymer the polymer-solvent ratios are often modified on drying or aging to result in an unpredictable composition of variable polymer chain length and disrupted spacing of reactive centers.

The uncontrolled expansion and contraction of the cellulose polymer strand is a serious problem for those polymer systems wherein a specific porosity or permeability is desired. This problem is especially serious when pore-size is determined by solvation with a volatile polar solvent such as water which upon drying disrupts the spacings between the amorphous and crystalline centres through contraction of the strand. When glycerin, sorbitol, polyethylene glycol or other similar glycol, or a polyhydric alcohol solvent is used their hygroscopic properties cause variations in polymer strand length on standing as water is absorbed into the system. The variations in the polymer chain spacing for the reaction hydrophilic centres become a special problem when cellulose compositions are prepared for use in the solid state as for example when solvated cellulose is used as a molecular screen to proportion or deliver quantities of a chemical from a reserve over an extended period of time.

Ideally, the solvent used in the system should cause the cellulose polymer strand to swell to a predetermined desired length and then enable the achieved expansion to be fixed so that the formed spacing is maintained irrespective of whether the solvent polymer ratio is modified or even if the solvating substance is removed. In such manner a solvated cellulose polymer matrix could be prepared with a predetermined porosity and permeability to enable the diffusion of selected substances from a reservoir for use in the dry, semi-solid or thixotropic state.

While the ability to fix a polymer chain length has been described for certain synthetic organic polymers, the means to accomplish such curing is not known for polysaccharides and most natural polymers. While the heat will cure thermo-sensitive synthetic polymer and it will denature a protein, heat destroys the polysaccharide structure. While ultraviolet light will serve as a curing agent for certain synthetic organic polymers, it is without effect on polysaccharides and may induce photo-synthetic chemical changes. Although specific curing agents are known to the art as being able to cure an expanded organic polymer chain, these are without value in accomplishing of this effect for a polysaccharide polymer chain especially such polymers as cellulose and derivatives.

The importance of a means to fix the distance between the crystalline and amorphous areas of a cellulose polymer to form a constant degree of pore-spaces and to also influence the availability of the hydrophilic centers of the polymer chain is readily appreciated when one considers the advantages of a bio-degradable molecular screen utilizing a cellulose polymer. Thus, if it is desired to prepare a cellulose polymer composition with a certain pore-spacing intended to confer a semi-permeability to a composition thereby permitting chemicals to be screened or diffused through the polymer composition at a specific rate per unit time and thereby control the release of essential fertilizing substances or pesticides at a rate consistent with their need, both waste due to excess and environmental poisoning are avoided.

In U.K. Pat. No. 1,405,088, there is described and claimed a matrix comprising an intimate mixture of a higher aliphatic alcohol, which is defined in the specification to be an aliphatic alcohol containing 8 to 18 carbon atoms which may be substituted by a further aliphatic group also containing 8 to 18 carbon atoms, and a water-soluble hydroxyalkyl cellulose hydrated to that extent which is produced by the addition of water between two and three times that of the dry weight of the hydroxyalkyl cellulose.

The process for the manufacture of the matrix described in that specification is a multistage process in which the hydrated cellulose and the higher aliphatic alcohol are each prepared in the form of granulates, and the granulates are them mixed together.

The disadvantages of this process are that it proceeds in a number of stages and that the extent of solvation of the cellulose is limited by the requirement of forming a granulate.

We have found according to the invention that if a cellulose polymer which has been solvated with a primary solvating agent, which may be water, but can be other solvents or mixtures of said solvents with water, as described herein, is reacted directly with the higher aliphatic alcohol, in particular by adding it to the molten alcohol, the two components unexpectedly react to form a coordination complex, which can be used as a matrix. This matrix or complex is distinguished from simple mixtures of the hydrated cellulose and the aliphatic alcohol, as is clearly shown by experiments which have been carried out which involve measurement of the electrical conductivities, which are described below.

When two or more substances are added to the same solvent, the specific electrical conductivity of a mixture will generally be expressed as the arithmetic sum of the number of dissolved particles in solution. However, if the number of particles in solution is changed because of an interaction between the solvent and the dissolved particles, or a reaction between the particles themselves which either increases or reduces the number of particles in solution, then this interaction is reflected as a change in the specific electrical conductance resulting for the solution when compared to the separate values.

If the specific electrical conductivity of a substance in solution is greater than the additive (arithmetic) sum of the separate electrical conductivity values determined for the individual components, the this shows that a solvation reaction has occured which activates a number of electrical centers of the particles in the solution thereby increasing the electrical conductivity of the solution. Such increased electrical conductance generally occurs when the process of solvation increases the particles in solution through ionization. The increase in specific electrical conductivity establishes the formation of a hydrogen bonded molecular coordination compound, which now causes an increase in ionizing centres of the new coordination complex through solvation.

On the other hand if the specific electrical conductivity value determined for two or more substances in solution is less than the arithmetic sum of the individual electrical conductivity values, then this is evidence of a decreased ionizing potential. Such decreased potential occurs through the formation of electron sharing internal hydrogen bonded, chelate coordination compounds. Such chelates exhibit a depressed ionization level for the formed compound since the hydrogen bonding ionizing centres are now blocked.

When the specific electrical conductivity of the compound in solution remains substantially the additive sum of the individual values determined for the separate moieties in solution, then this is evidence that no interaction has occurred and that the solvation process has not altered the internal bonding of the moieties in solution. Such molecules do not ionize into component parts and generally behave as uncomplexed, simple mixtures.

Thus, through the determination of the specific electrical conductivity of materials in solution, the formation and structure of a new molecular coordination compound may be readily established as well as the nature of its electrical bonding that is, whether it is an internal hydrogen bonded chelate cordination complex or a hydrogen bonded solvation complex.

Measurement of the specific electrical conductivity of the materials which we have studied was carried out with a modified Wheatstone Bridge Assembly. The resistance to the flow of electrical current (ohms) was determined for a specific volume of the test solution and the specific conductance of teh solution being tested was computed as the reciprocal of the specific electrical resistance for the solution and is expressed in units termed, "mhos", (the reciprocal of ohms).

The conducting power of the molecules in solution was therefore expressed in terms of specific conductance, as the reciprocal of the ohms (mhos) measured for a solution containing a specific gram-molecular fraction of solute. The conducting power of the solution was recorded as the flow of current between parallel electrodes, 1 cm apart and the specific conductance (L) is computed from the resistance (R) divided into the cel constant (K) and is expressed as "mhos/cm."

Water was used as the polar solvent (primary solvating agent) to determine the specific electrical conductivity of the separate compositions tested because of its high di-electric constant of 78.5.

The materials studied were those described in Example 1 set out later.

The specific electrical conductance of hydroxyalkylcellulose (as well as hydroxymethylcellulose, hydroxyethylcellulose and hydroxypropylcellulose) was determined to establish a base value. The effect of water solvation on the specific electrical conductance of the selected hydroxyalkylcellulose dispersion was followed and correlated with the gelation process reflected by increasing penetrometer unit values over the range of from 100 to 800 units. The increased gelation of an aqueous hydroxyalkylcellulose solution was a function of cellulose fibre expansion.

Hydroxymethylcellulose (10 gms) was dispersed in an equal part by weight of water as described in step 1 of Example 1. In this case fresh double-distilled water was used. The specific electrical conductivity for the cellulose dispersion was determined immediately after addition of the cellulose to the solvent and at appropriate intervals thereafter determined by a change in the gel consistency of the dispersion reflected by penetrometer measurement over the range of 100 to 800 penetrometer units.

The specific electrical conductivity of hydroxyethylcellulose and hydroxypropylcellulose utilizing the same method and parts by weight described above was also determined.

A $2.5 \times 10^{-3}$ molar aqueous concentration of the respective hydrated hydroxyalkylcellulose gel was used in the measurement of the specific electrical conductance.

TABLE 1
SPECIFIC ELECTRICAL CONDUCTANCE* OF HYDROXYALKYL CELLULOSE GELS

| Compound | Start | Gel Penetrometer Units/10 Second Interval | | | | |
|---|---|---|---|---|---|---|
| | | 100 (MHOS) | 200 (MHOS) | 300 (MHOS) | 500 (MHOS) | 800 (MHOS) |
| Hydroxymethyl-cellulose | nil | $1.6 \times 10^{-4}$ | $2.8 \times 10^{-4}$ | $2.9 \times 10^{-4}$ | $3.2 \times 10^{-4}$ | $4.1 \times 10^{-4}$ |
| Hydroxyethyl-cellulose | nil | $1.6 \times 10^{-4}$ | $2.9 \times 10^{-4}$ | $3.2 \times 10^{-4}$ | $3.6 \times 10^{-4}$ | $3.9 \times 10^{-4}$ |
| Hydroxypropyl-cellulose | nil | $1.8 \times 10^{-4}$ | $2.7 \times 10^{-4}$ | $3.0 \times 10^{-4}$ | $3.3 \times 10^{-4}$ | $3.8 \times 10^{-4}$ |
| Water | nil | — | — | — | — | — |

*The values are expressed as MHOS, the reciprocal of resistance (OHMS)

The specific electrical conductivity of the hydroxymethylcellulose aqueous solution (Table I) demonstrates a hydrogen bonded solvation reaction. The specific electrical conductance increases as the cellulose polymer strand expands to expose more reactive hydrophilic ionizing centres which interact with the aqueous solvent.

The above experiment was then repeated with differing ratios of primary solvating agent to cellulose compound in order to evaluate the effect of greater amount solvent on the solvating action of the cellulose component. Within the range of from 1 to 6 parts by weight of water for each part by weight of cellulose compound, the specific electrical conductivity determined for the particular gel consistency described in Table I was essentially the same. (see Table II). However, the time necessary to achieve the respective gelation consistency was increased directly with the increase in the protection of solvent.

TABLE II
THE EFFECT OF VARYING PROPORTIONS OF SOLVENT TO CELLULOSE COMPONENT (HYDROXYMETHYLCELLULOSE) ON THE SOLVATION REACTION

| Solvent | Ratio of Solvent to Cellulose (w/w) | Start | Gel Consistance-Penetrometer Units | | |
|---|---|---|---|---|---|
| | | | 100 (a) | 300 (a) | 500 (a) |
| Water | 2:1 | nil | $2.2 \times 10^{-4}$ | $2.7 \times 10^{-4}$ | $3.9 \times 10^{-4}$ |
| Water | 3:1 | nil | $2.3 \times 10^{-4}$ | $2.8 \times 10^{-4}$ | $3.8 \times 10^{-4}$ |
| Water | 4:1 | nil | $2.3 \times 10^{-4}$ | $2.8 \times 10^{-4}$ | $3.6 \times 10^{-4}$ |
| Water | 6:1 | nil | $2.7 \times 10^{-4}$ | $2.9 \times 10^{-4}$ | $3.7 \times 10^{-4}$ |

(a) The values are expressed as MHOS, the reciprocal of resistance (OHMS)

The first experiment was then repeated in which in place of pure water there were used aqueous ethanol solutions (1%, 10% and 25% by weight solution of ethanol in water) as the hydrating solvent. In general, the magnitude of specific electrical conductivity remained the same (see Table III), but the time to achieve the indicated gel consistency was modified so that the time evolved to achieve a determined gelation consistency was more rapid at the lower ethanol concentrations, but slowed at the higher concentrations of ethanol.

TABLE III
THE EFFECT OF AQUEOUS ALCOHOL ON THE SOLVATION REACTION[a] OF HYDROXYALKYL-CELLULOSE (HYDROXYMETHYLCELLULOSE)

| Solvent | Start | Gel Consistency-Penetrometer Units | | |
|---|---|---|---|---|
| | | 100 (MHOS) | 300 (MHOS) | 500 (MHOS) |
| Ethanol (1%) Water (99%) | nil | $2.6 \times 10^{-4}$ | $3.0 \times 10^{-4}$ | $3.9 \times 10^{-4}$ |
| Ethanol (10%) Water (90%) | nil | $2.6 \times 10^{-4}$ | $3.1 \times 10^{-4}$ | $3.8 \times 10^{-4}$ |
| Ethanol (25%) Water (75%) | nil | $2.7 \times 10^{-4}$ | $3.2 \times 10^{-4}$ | $3.7 \times 10^{-4}$ |

[a] The solvent ratio to cellulose component was equal parts by weight of solvent and cellulose.

The increased specific electrical conductance observed for the hydrated hydroxyalkylcellulose polymer appears to be a function of hydrogen bonded solvation since the electrical conductance observed for the hydrated cellulose polymer is greater than that observed for the solvent alone.

The specific electrical conductivity of a series of higher aliphatic alcohols ($C_{12}$-$C_{18}$) was then determined. The aliphatic alcohols studied were: lauryl alcohol ($C_{12}H_{25}OH$), myristyl alcohol ($C_{14}H_{24}OH$), cetyl alcohol ($C_{16}H_{23}OH$) and stearyl alcohol ($C_{18}H_{37}OH$).

In all instances the specific electrical conductivity was nil.

The effect of the higher aliphatic alcohol ($C_{12}$–$C_{18}$) on the solvation reaction of the hydroxyalkylcellulose component was studied by comparing the specific electrical conductance obtained for the individual cellulose compound with that obtained for the combined hydroxyalkylcellulose and higher aliphatic alcohol. The ratio of the hydroxyalkylcellulose to the higher fatty alcohol studied was 1:2; 1:3 and 1:4 parts by weight.

The appropriate hydroxyalkylcellulose was hydrated in the manner described in Example 1, Step 1 and the specific electrical conductivity determined at immediately after adding; and at room temperature. The appropriate fatty alcohol was then melted and the specific electrical conductivity measured. In accord with the procedure of Example 1, Step 2, the hydrated cellulose was added to the molten alcohol and the specific electrical conductance for the combination determined immediately after adding the hydrated cellulose. When the temperature of the mass was at room temperature, the specific electrical conductivity was again measured. (See Table IV).

TABLE IV

THE EFFECT OF A MOLTEN FATTY ALCOHOL ON THE SPECIFIC ELECTRICAL CONDUCTANCE OF SOLVATED HYDROXYALKYLCELLULOSE (HYDROXYMETHYLCELLULOSE)

| Fatty Alcohol | Ratio of Alcohol to Cellulose Component[b] | Aliphatic Alcohol/Cellulose Combination[a] Specific Electrical Conductance (MHOS) | |
|---|---|---|---|
| | | Molten State | Room Temperature |
| Lauryl Alcohol | 2:1 | $2.1 \times 10^{-4}$ | $2.4 \times 10^{-4}$ |
| Lauryl Alcohol | 3:1 | $2.2 \times 10^{-4}$ | $2.3 \times 10^{-4}$ |
| Lauryl Alcohol | 4:1 | $2.1 \times 10^{-4}$ | $2.3 \times 10^{-4}$ |
| Myristyl Alcohol | 2:1 | $2.2 \times 10^{-4}$ | $2.2 \times 10^{-4}$ |
| Myristyl Alcohol | 3:1 | $2.2 \times 10^{-4}$ | $2.3 \times 10^{-4}$ |
| Myristyl Alcohol | 4:1 | $2.1 \times 10^{-4}$ | $2.1 \times 10^{-4}$ |
| Cetyl Alcohol | 2:1 | $2.3 \times 10^{-4}$ | $2.3 \times 10^{-4}$ |
| Cetyl Alcohol | 3:1 | $2.3 \times 10^{-4}$ | $2.1 \times 10^{-4}$ |
| Cetyl Alcohol | 4:1 | $2.1 \times 10^{-4}$ | $2.1 \times 10^{-4}$ |
| Stearyl Alcohol | 2:1 | $2.4 \times 10^{-4}$ | $2.2 \times 10^{-4}$ |
| Stearyl Alcohol | 3:1 | $2.2 \times 10^{-4}$ | $2.1 \times 10^{-4}$ |
| Stearyl Alcohol | 4:1 | $2.1 \times 10^{-4}$ | $2.2 \times 10^{-4}$ |

[a]The product described is the composition obtained as a result of Step 2 of Example 1. The hydroxymethylcellulose had been hydrated with water (Step 1) and was used at a Gel penetrometer value of 200 units. For reference purposes the specific electrical conductivity of the hydroated hydroxymethylcellulose, with a gel consistency of 200 penetrometer units, is $2.8 \times 10^{-4}$ mhos.

It was readily apparent that the combination between the hydroxyalkylcellulose and the molten fatty alcohol results in a termination of the solvation reaction as demonstrated by the sharp fall in specific electrical conductivity. Moreover, the new conductance value observed does not materially change when the composition solidifies at room temperature.

It is important to note that the specific electrical conductivity value of the combined hydroxyalkylcellulose and fatty alcohol is less than the arithmetic sum of the solvated hydroxyalkylcellulose component, but greater than the sum of the separate conductance values for the respective substances. Thus it has been found that both the fatty alcohol and the hydroxyalkylcellulose separately showed virtually no specific electrical conductivity, whereas when these are combined a specific conductance value of $2.1 \times 10^{-4}$ is obtained. This value is greater than the arithmetic sum of the individual values and suggest that a hydrogen bonded coordination complex was formed. The new molecular complex has physical properties that were not observed for the respective separate materials in the uncombined state. This response increase in conductivity parallels that observed after the solvation of the hydroxymethylcellulose with the strongly polar water solvent.

However since the cellulose component had already been solvated (with water at Step 1, above) to form a hydrogen bonded coordination compound, then the effect of the fatty alcohol was apparently to displace the hydrogen bonded aqueous solution and the nature of the new bond formed has to be measured against the solvated hydrated cellulose and the fatty alcohol. (See Table V). When the specific electrical conductivity values for the solvated hydroxyalkylcellulose was compared with the value obtained after combination with the fatty alcohol, it was found that there is a decrease in the specific electrical conductivity for the combination. This is proof of the formation of a new internal molecular hydrogen bonded coordination complex. Thus while the high fatty alcohol serves to displace, in part, the solvated hydrogen bonded water units to form a secondary solvated hydrogen bonded complex, the structure of this new complex appears to be that of an internal molecular chelate structure formed by blocking ionizing centres. This new internal chelate structure is maintained in the solid state, as demonstrated by the virtually unchanged specific electrical conductivity determined at room temperature.

In a further experiment one part by weight of hydrated hydroxymethylcellulose (No. 16 standard mesh particle size) was mixed with two parts by weight of the stearyl alcohol (No. 16 standard mesh particle size). The simple mixture was then added to 20 ml. of distilled water and the specific electrical conductivity determined immediately after addition.

An equal weight of the granulate complex obtained as a result of Example 1, Step 3, which had been shown as demonstrated above to be an internal molecular hydrogen bonded chelate, was added to the 20 ml of water and the specific electrical conductivity again determined. (See Table V).

TABLE V

THE COMPARATIVE SPECIFIC ELECTRICAL CONDUCTIVITY OF A SIMPLE MIXTURE AND THE FORMED CHELATE COORDINATION COMPLEX

| Composition* | Specific Electrical Conductivity (MHOS) | | |
|---|---|---|---|
| | Start | 10 min. | 1 hour |
| SIMPLE MIXTURE GRANULATE | | | |
| Hydroxymethylcellulose (1 part) + Stearyl Alcohol (2 parts) | nil | $2.6 \times 10^{-4}$ | $3.8 \times 10^{-4}$ |
| CHELATE COORDINATION COMPLEX | | | |
| Hydroxymethylcellulose (1 part) | | | |

TABLE V-continued
THE COMPARATIVE SPECIFIC ELECTRICAL CONDUCTIVITY OF A SIMPLE MIXTURE AND THE FORMED CHELATE COORDINATION COMPLEX

| Composition* | Specific Electrical Conductivity (MHOS) | | |
|---|---|---|---|
| | Start | 10 min. | 1 hour |
| { (Stearyl Alcohol (2 parts) } | $2.2 \times 10^{-4}$ | $2.1 \times 10^{-4}$ | $2.3 \times 10^{-4}$ |

*1 gram sample of each composition was dispersed in 20 ml. of water.

These results clearly show that there is a new molecular coordination complex formed between the cellulose polymer and the high aliphatic alcohol. A particular example of this complex is the cured matrix which is the product of Example 1.

It is believed that this new coordination complex is formed through two sequential actions. The first, involves the solvation of hydroxyalkylcellulose to form a hydrogen bonded coordination complex which serves as a precursor to the second action solvation displacement to result in the internal molecular chelate coordination complex between the higher aliphatic alcohol and the cellulose component.

The solvation of the cellulose component thus actuates the hydrophilic hydrogen bonding centers of the cellulose to serve as a seed substrate for the second action. The higher fatty alcohol then displaces the hydrogen bonded polar solvent from the cellulose centers to form a new fatty alcohol complex. However, because of the particular steric properties of the long chain hydrocarbon portion of the high aliphatic alcohols, the cellulose component forms an internal chelate bonded structure rather than a linear coordination complex such as formed with the small polar solvent units.

The invention therefore provides as a novel product a molecular coordination complex between a cellulose polymer and a solid aliphatic alcohol containing 8 to 18 carbon atoms optionally substituted with an aliphatic group containing 8 to 18 carbon atoms.

In another aspect of the invention there is also provided as a novel product a cellulose polymer which has been solvated with a volatile polar solvent, wherein the volatile polar solvent has been at least partially replaced by a solid aliphatic alcohol in such a manner that a molecular coordination complex is formed.

The invention also provides a process for the preparation of a complex or matrix according to the invention in which the cellulose polymer is solvated with a primary solvating agent and the solvated cellulose polymer is mixed with the solid aliphatic alcohol to displace the primary solvent and form the molecular coordination complex or matrix.

The process for the production of the coordination complex or matrix involves direct reaction of the solvated cellulose with the aliphatic alcohol without any intermediate granulation step.

It is in principle a one step process leading to novel products which are very stable and which can be made to have a variety of porosities as more fully described below.

The products according to the invention are dry free-flowing cured cellulose polymers having a defined spacing which may be maintained, for a very long time; in practice periods of time in excess of three years, are not unusual.

The distances between the amorphous and crystalline regions to form the pores and the spacing of the hydrophilic reactive centers of the cellulose which makes possible further solvation reactions are preserved at their determined levels through the method of manufacture described herein. Thus according to the invention a cellulose polymer may now be solvated to a predetermined state to achieve a desired porosity and then cured with the solid aliphatic alcohol so that aging and/or drying does not disturb the formed permeability of the expanded cellulose polymer, thereby providing a stable molecular screen to control the diffusion of substances for an extended time period.

In carrying out the invention, an alkyl cellulose polymer in which the alkyl group is from 1 to 4 carbon atoms in chain length; a hydroxyalkyl cellulose polymer in which the hydroxyalkyl group is from 1 to 4 carbon atoms in chain length; a cellulose ester; a cellulose ether; a carboxyalkyl cellulose compound in which the alkyl group is from 1 to 4 carbon atoms in chain length, or a mixture of these, is solvated with a volatile polar solvent to a desired degree of swelling, and the expansion of the solvated cellulose polymer is preserved by reacting the expanded polymer with a solid non-polar aliphatic alcohol of the formula ROH in which R is an alkyl group of preferably 10 to 18 carbon atoms in chain length to displace the volatile polar solvent from its hydrogen-bonded center, so that a curing action of the solvated cellulose polymer is obtained. This curing action of the expanded swollen cellulose polymer by the solid alcohol occurs as a result of new hydrogen bond formation between the hydrogen atom of the aliphatic alcohol and the oxygen of the hydrophilic center of the polymer the new internal molecular hydrogen-bonded coordination complex which because of its new structure retains its expanded polymer length even in the solid state.

In practice the expansion of the selected cellulose polymer chain to a desired pore spacing is achieved according to the invention by solvating the cellulose polymer with a volatile polar solvent. By the term volatile polar solvent is meant water or aliphatic alcohol of the formula ROH in which R is an alkyl group of from 1 to 4 carbon atoms in chain length or a ketone of the formula RCOR in which R has the meaning given, in particular, acetone or methyl ethyl ketone. Mixtures of such volatile solvents may also be used. Where the volatile polar solvent is an alcohol-water mixture of the ratio of alcohol to water in the solvent mixture is from 1 to 50 parts by volume of alcohol for each part by volume of water. The range in the proportion of polar solvent used to solvate the cellulose polymer is from 1 part by weight of cellulose polymer to from 1 to 6 parts by weight of solvent. The selected cellulose polymer is added to the desired solvent in small increments and the solvation process is allowed to proceed over a period of from fifteen minutes to one hour depending upon the extent of polymer-solvating desired to provide optimal porosity and permeability for most uses.

The use, as the polar volatile solvent, of an organic solvent as specified above, either as such or with water has advantages over water, since the amount of time and energy involved in drying the final product can be reduced. The use of such solvents as such or in admixture with water may indeed be preferred.

In preparing the products according to the invention proper solvation of the cellulose polymer with the volatile polar solvent is important so that it has a particular consistency before it is reacted with the aliphatic alcohol. This consistency is preferably determined by means of a cone or needle penetrometer in which the depth of the penetration of the weighed cone is measured for a given time of interval, such as, for example, 10 seconds. An instrument which is suitable to be used for this purpose is the Stanhope Penetrometer which is well known in the art and is described for example in Sherman, P: Industrial Rheology and Rheological Structures, Wiley, New York, 1949; Van Wazer JR, et al: Viscosity and Flow Measurement, Interscience, New York, 1963 and Martin AN, et al., In Bean HS, et. eds: Advances in Pharmaceutical Sciences, Vol. 1, Academic, London and New York, 1964, and comprises a cone or needle attached to a holding rod which, when released, plunges vertically into the sample under the influence of its own, known, weight. A stop-watch is triggered to measure the time interval for penetration and the consistency of the mass is expressed in the depth of penetration units observed. The consistency of the solvated hydroxymethylcellulose using water as the polar solvent should be within the range of 100 to 800 penetrometer units, preferably 100 to 500 such units.

When the cellulose polymer has been solvated with the primary polar solvent it is added to a melt of the selected solid aliphatic alcohol of the formula $R^1OH$ in which $R^1OH$ is an alkyl group with a carbon chain length of from 8 to 18 carbon atoms (which may be substituted with an aliphatic group of from 8 to 18 carbon atoms), but preferably an alkyl group with a carbon chain length of 10 to 18 carbon atoms and the whole is stirred until the temperature of the composition returns to room temperature. The amount of aliphatic alcohol used to cure the solvated polymer is preferably approximately equal in parts by weight to the parts by weight of the primary polar solvating fluid used to swell the cellulese polymer strand. When the amount of solid non-polar aliphatic alcohol used to cure the cellulose polymer is less than the weight of primary solvating agent then incomplete curing results, with variation in pore size spacing as the solvated polymer composition dries. When an excess quantity of solid non-polar aliphatic alcohol is used a matrix rigidity of the cellulose fibre strand results so that the spacing between the crystalline regions is reduced and the screening power of the formed matrix is diminished.

The solid non-polar aliphatic alcohol with a carbon chain length of from 8 to 18 carbon atoms that is preferably used to cure the polymer may be either saturated or non-saturated and of straight or branched chain. Preferred alcohols are lauryl, myristyl, cetyl and stearyl alcohols or mixtures thereof. One may however use an alcohol with a side chain aliphatic group containing from 8 to 18 carbon atoms. A representative alcohol of this type is cetostearyl alcohol.

The selected aliphatic alcohol is melted at a temperature not exceeding 70° C. and the solvated cellulose polymer added to the molten alcohol in small increments with stirring to insure a uniform dispersion. When the hydrogen-bonded reaction product formed between the solvated cellulose polymer and the molten aliphatic alcohol has cooled to room temperature the displacement reaction is virtually complete and the displaced solvating agent may now be removed by drying.

The new formed hydrogen-bonded compound is preferably allowed to air-dry although any drying means may be used. It may be found preferable to screen the mass through a standard mesh size screen such as are well known to the art in order to obtain a granular particle graded in size of from 2.36 mm to 850 $\mu$m in particle size (US Standard Mesh No. 8 to No. 20). The drying process may be accelerated through the use of vacuum and/or heat or a combination of these.

When it is desired to vary the pore spacing of the cellulose polymer strand then different proportions of primary polar solvating agent to cellulose polymer are used and a preferred range in amount of solvating agent to cellulose polymer is from 1 to 6 parts by weight of primary solvent for each part by weight of cellulose polymer used. This range of solvating agent to cellulose polymer will determine the characteristics of the cured cellulose polymer matrix as a molecular screen in the solid state. Thus when the proportion of solvating agent to cellulose polymer is 1:1 only a minimal screening retention is provided and the swelling capacity of the cellulose polymer is such that the hydrogen-bonded crystalline linkages has not been effected since solvation is only at an intervening level.

However, when a ratio of 2 to 4 parts by weight of primary solvating agent for each part of cellulose polymer is used then a proportionate desired level of desegregation of the cellulose polymer is observed. This increases the pore spacing as the solvating fluid ratio increases and permits a better control diffusion of compounds through the cured matrix.

When the proportion of the primary solvating agent to cellulose polymer is from 5 to 6 parts by weight of solvating agent for each part by weight of cellulose polymer then desegregation is more pronounced and pore formation is now reduced. This reduction results in a marked inhibition of diffusion of chemical substance through the solid matrix since more hydrogen-bonded centres are now formed with the solven to cause a blockade. The duration of the solvation process is not critical provided that the proper consistency, measured by the penetrometer is attained and generally a period of from fifteen minutes to one hour is utilized but no difference in effect is seen when longer periods are utilized.

The cured cellulose polymer matrix may be used in combination with substances such as for example a catalyst for a chemical reaction; a pharmaceutically active agent; active chemical agents; agricultural fertilizers; dyestuffs; corrosion inhibitors as well as other active substances. When such compositions containing the cured cellulose polymer matrix and an active substance are desired then the cured cellulose polymer matrix should be used in an amount of not less than 20 percent by weight of the total weight of the finished unit composition in order that a preferred release rate of the desired active substance occurs.

It has been found that when the cellulose polymer composition was less than 20 percent by weight of the total of the finished unit composition the control of the rate of release of active compound contributed by the cured cellulose polymer matrix was less than optimal but when the amount of cured cellulose polymer composition was greater than 20 percent by weight of the finished unit composition then an increased slowing in the release rate resulted. Thus, quantities of 25 percent and 30 percent and up to 90 percent by weight of the cellulose polymer composition may be used in order to control the release of certain substances over extended periods of time. Such controlled release rates become most desirable when the addition of catalyst and/or reagents to a chemical reaction is required over an extended period of time as for example where an exothermic reaction occurs as the result of the inter-reaction of two chemical substances and it is preferred to add one of the reagents in small increments to avoid an explosion. Through the use of a controlled release matrix system as described above the compatible catalyst and/or compatible chemical reagent may be incorporated with the cured cellulose polymer to be released in small increments over a desired period and the exothermic reaction may be fully controlled with appropriate conventional heat-transfer systems.

The cured cellulose polymer matrix according to the invention is particularly suitable for incorporation in controlled release preparations for use in the controlled administration of pharmaceutically active substances. The matrix is suitable, in particular, for incorporation in solid controlled release preparations for oral administration, controlled release suppositories, controlled release creams and ointments for topical administration, and controlled release emulsions and other liquid preparations for oral or topical administration.

The invention also provided a process in which the solvated cellulose polymer is introduced directly into a melt of the solid aliphatic alcohol.

Although the desired active substance may be added directly to the cured cellulose polymer composition it may be found desirable to utilize other substances which serve specific functions in the manufacture of a finished unit composition or to facilitate the handling of materials. Thus for example lactose, starch and talc may be used as diluents in suitable amounts required for a specific composition and such substances as petrolatum and magnesium stearate may be added to provide a slip to a powder or granule in order to facilitate its flow through mechanical processing equipment such as punch presses, conveyer systems and extrusion apparatus.

The invention will now be further described with reference to the following Examples, (in these Examples the formation of new molecular coordination complexes was verified by electrical conductivity measurement as described above).

EXAMPLE 1

Step 1:
10 g of hydroxymethylcellulose was added in small increments to 10 g of water contained in a suitable vessel at room temperature or gently warmed, preferably to a temperature not exceeding 70° C. The mixture was stirred until a uniform paste resulted with a consistency of from 100 to 500 penetrometer units per 10 second interval at 25° C. measured with a Stanhope Penetrometer in combination with a cone-shaped, 7.5 g metal plunger.

Step 2:
The hydrated hydroxymethylcellulose polymer was added to a melt of 20 g of stearyl alcohol and the composition was stirred while the mass hardened and the temperature returned to room temperature (about 25° C.).

Step 3:
The composition was granulated through a 1.18 mm mesh screen (U.S. Standard No. 16) and dried so that the moisture content of the granules was less than 0.1 percent.

The resultant dried composition comprised the new hydrogen-bonded compound formed between hydroxymethylcellulose and stearyl alcohol which had a uniform porosity and could be used as a matrix to control the release of pharmacologically active ingredients in tablet, capsule or pellet dosage form.

The hydroxymethylcellulose described above may be replaced by hydroxyethylcellulose, hydroxypropylcellulose and hydroxybutylcellulose, which are used in the same amounts by weight.

In place of the stearyl alcohol there may be substituted in equal amounts by weight another solid aliphatic alcohol of the formula ROH, in which R represents an alkyl group containing from 10 to 18 carbon atoms.

EXAMPLE 2

100 g of a methyl cellulose polymer was added to 300 g of water in a suitable vessel, and the mixture was stirred until a granular paste was obtained with a consistency of from 100 to 150 penetrometer units per 10 second interval at 25° C. when measured with a Stanhope Penetrometer in combination with a cone-shaped 7.5 g metal plunger.

The hydrated methyl cellulose polymer was added to 300 g of molten cetostearyl alcohol and the whole blended well until the mass cooled to about 25″ C. The solid mass was allowed to set and then granulated through a 1.18 mm mesh screen (U.S. Standard No. 16) and dried.

The composition formed may now be used in further manufacture of finished dosage units such as tablets, capsules or pellets intended to control the rate of release of a selected active ingredient.

In place of the methyl cellulose compound described above there may be substituted in the same amounts by weight an alkyl cellulose compound in which the alkyl group contains from 2 to 4 carbon atoms or a carboxyalkylcellulose compound in which the alkyl group contains from 1 to 4 carbon atoms.

In place of the cetostearyl alcohol described above, there may be substituted in equivalent amounts by weight, a solid aliphatic alcohol of the formula ROH, in which R represents an alkyl group of from 10 to 18 carbon atoms in chain length.

EXAMPLE 3

25 g of a cellulose ether was added to 100 g of water in a suitable container fitted with a stirrer. The mixture was stirred until a granular paste was obtained, with a consistency of from 100 to 150 penetrometer units per 100 second intervals at 25° C. when measured with a Stanhope Penetrometer in combination with a cone-shaped 7.5 g metal plunger.

The hydrated cellulose ether was then added to 100 g of molten myristyl alcohol and the whole blended well until the mass cooled to room temperature.

The mixture was allowed to set and then granulated through a 1.18 mm mesh screen (U.S. Standard No. 16) and dried.

The composition formed may be now used in further manufacture of finished dosage units such as tablets, capsules or pellets, intended to control the rate of release of a selected active ingredient.

In place of the cellulose ether described above there may be substituted in the same amounts by weight a cellulose ester.

In place of the myristyl alcohol described above there may be substituted in the same amounts by weight a solid aliphatic alcohol of the formula ROH, in which R represents an alkyl group of from 10 to 18 carbon atoms in chain length.

EXAMPLE 4

In place of the water used as a polar solvating agent in Examples 1, 2 and 3, there may be substituted in equivalent amounts by weight of a 50 percent aqueous methanol solution a 50 percent aqueous acetone solution or a 50 percent aqueous methyl ethyl ketone the remainder of the steps being the same.

EXAMPLE 5

Example of a method of preparing a unit dosage form to control the release of a desired active substance, for example a pharmaceutically active substance.

Step 1:

An appropriate quantity of formed cured cellulose polymer-high alkyl alcohol compound obtained in any of Examples 1 to 4 above was mixed with the appropriate quantity of active ingredient and diluents. The proportion of the cured cellulose polymer was from 20 to 30% by weight of the total weight of the unit dosage form, to obtain sustained release of the selected active ingredient. Thus, for example, when the weight of the cured cellulose polymer was about 20% by weight of the finished dosage form, then the release of the active ingredient was sustained over a period of 4 hours. However, when the proportion of cured cellulose polymer was 25% by weight of the finished dosage form, the release of the compound occurred over a period of 7 hours and amounts greater than 30% by weight resulted in a release period of about 10 hours. The cured polymer could be used in amounts up to 90% by weight of the finished unit weight for special preparations.

Adjustment of the proportion of the cured polymer was achieved by means of conventional, accepted diluents such as lactose and talc, which were added in the desired amounts to bring the unit dosage formula to the proper weight.

Step 2:

The desired quantity of the selected active ingredient was mixed with the appropriate amount of lactose or talc as a diluent, the amount of diluent being sufficient to provide a unit dose of proper weight so that the proportion of the weight of the cured cellulose polymer to the total weight of the unit dose was within the critical limit required to obtain the desired predetermined rate of release of the active ingredient.

Step 3:

The blend of active ingredient and diluent was added to the product obtained from Step 1; the whole was mixed well and granulated through a 1.18 mm mesh screen (No. 16 U.S. Standard) and then formed into the preferred unit dose as for example, tablets, capsules and/or pellets.

EXAMPLE 6

To prepare a delayed release tablet of potassium chloride the following procedure was used:
Potassium chloride: 820 g
Cured hydroxyethylcellulose: 185 g
Talc: 150 g Manufacturing Procedure Step 1:
The potassium chloride and talc were blended.
Step 2:
The blend of Step 1 was added to the cured hydroxyethylcellulose, obtained according to Example 1 above, and granulated through a 1.18 mm stainless steel standard mesh screen (U.S. Standard No. 16). Necessary lubricants were added, if required, and the granules compressed into tablets of suitable size and shape, each having a unit weight of about 750 mg.

EXAMPLE 7

Prednisolone: 75 g
Lactose: 10 g
Cured methylcellulose compound: 15 g
Step 1:
The prednisolone, talc and cured methylcellulose, obtained according to Example 1 above, were blended in a suitable vessel and granulated through a 1.18 mm mesh screen (U.S. Standard No. 16).
Step 2:
The granulate obtained according to step 1 was compressed into tablets of suitable size and shape to provide a tablet with the unit dose of 5 mg. of prednisolone and a proportion of cured methylcellulose by weight of 30 percent of the total weight of the tablet.

EXAMPLE 8

Aspirin: 300 g
Cured carboxyethylcellulose: 200 g
Lactose q.s.: 1 kilogram
Step 1:
All of the ingredients were mixed in a suitable vessel and blended well. When a uniform distribution was obtained, the whole was granulated through a 1.18 mm mesh screen (U.S. Standard No. 16) and compressed into tablets of suitable size and shape, so that each tablet contained 300 mg. of aspirin, 20% by weight of the total weight of the tablet being cured carboxyethylcellulose.

EXAMPLE 9

Nitroglycerin, 1:10: 16 g
Cured hydroxypropylcellulose: 30 g
Lactose: 38 g
Talc: 15 g
Step 1:
The ingredients were combined in a blender, mixed until a uniform distribution was obtained and granulated through a 1.18 mm mesh screen (U.S. Standard No. 16).
Step 2:
Tablet lubricants (magnesium stearate and talc) were added in a suitable quantity if needed and the mixture was compressed into tablets of suitable size and shape.

The release of nitroglycerin from the above tablet extended to a period of from 9 to 10 hours.

EXAMPLE 10

Cured hydroxyethylcellulose: 25 g
Aminophylline: 73 g

Tablet lubricants: 2 g

Step 1:

Aminophylline and the cured hydroxyethylcellulose were mixed until a uniform blend resulted and the blend was then granulated through a 1.18 mm mesh screen (U.S. Standard No. 16).

Step 2:

The tablet lubricants were added and the granulated was compressed into tablets of suitable size and shape or filled into appropriate gelatin capsules.

EXAMPLE 11

Suitable capsules and/or pellets useful to provide a sustained release of the selected active ingredient, as for example, the active ingredients described in Examples 5 to 10, may be prepared by filling the granules obtained prior to the tablet compression step, into suitable capsules, maintaining the critical ratio of the weight of cured cellulose polymer to the total weight of the capsule contents as follows:

(a) When the proportion of the cured cellulose polymer is 20% by weight of the weight of the capsule contents, then the release of the selected active ingredient will be extended over a period of about 5 hours.

(b) When the weight of the cured cellulose polymer is 25% of the weight of the capsule contents, then the release of the active ingredient is extended to about 7 hours.

(c) When the weight of the cured cellulose polymer is 30% of the total formula weight, then the release of the active ingredient will be between 9 to 10 hours.

(d) Under certain conditions, as for example, in chemical synthesis, it will be found desirable to employ a ratio of the weight of the cured cellulose polymer which is 90% by weight of the weight of the formulation used to obtain extended controlled release of a substance for more than 15 hours.

I claim:

1. A molecular coordination complex of a cellulose polymer and a solid aliphatic alcohol selected from the group consisting of unsubstituted solid aliphatic alcohols of 8-18 carbon atoms and solid aliphatic alcohols of 8-18 carbon atoms substituted by an aliphatic group of 8-18 carbon atoms.

2. Molecular coordination complex of claim 1 wherein said cellulose polymer is a hydroxy alkyl cellulose.

3. Molecular coordination complex according to claim 1 wherein the number of carbon atoms of the solid aliphatic alcohol is between 10 and 18 carbon atoms.

4. Molecular coordination complex according to claim 1 wherein said cellulose polymer is hydroxymethyl cellulose, hydroxyethyl cellulose or hydroxypropyl cellulose and wherein the aliphatic alcohol is lauryl, myristyl, cetyl, stearyl or cetostearyl alcohol.

5. Controlled release pharmaceutical composition comprising an active pharmaceutical agent distributed in the molecular coordination complex of claim 1.

6. Composition according to claim 5 wherein the amount of said molecular coordination complex is more than 20% of the weight of the composition.

7. Method of producing the molecular coordination complex of claim 1, which comprises solvating the cellulose polymer with a volatile polar solvent therefor to form a solvated cellulose polymer and reacting the thus solvated cellulose polymer with said solid aliphatic alcohol, thereby forming said molecular coordination complex.

8. Method according to claim 7 wherein said solvated cellulose polymer is introduced into a melt of said solid aliphatic alcohol so as to cause reaction therebetween, cooling the thus formed reaction mass and drying the same to remove any residual volatile polar solvent.

9. Method according to claim 8 wherein 1-6 parts by weight of said volatile polar solvent are used per each part of said cellulose polymer.

10. Method according to claim 8 wherein one part of aliphatic alcohol is used per each part of said volatile polar solvent.

11. The molecular coordination complex of claim 1 wherein said complex is porous.

* * * * *